United States Patent [19]

Riffle et al.

[11] Patent Number: 4,689,383
[45] Date of Patent: Aug. 25, 1987

[54] HYDROXYL-FUNCTIONAL DISILOXANES AND POLYSILOXANE OLIGOMERS

[75] Inventors: Judy S. Riffle; Iskender Yilgor, both of Oakland, Calif.

[73] Assignee: Thoratec Laboratories Corp., Berkeley, Calif.

[21] Appl. No.: 840,843

[22] Filed: Mar. 18, 1986

[51] Int. Cl.$^4$ ............................................. C08G 77/06
[52] U.S. Cl. ........................................ 528/12; 528/23; 528/25; 528/28; 528/29; 528/33; 528/37; 525/474; 556/423; 556/445; 556/449
[58] Field of Search ................... 556/423, 445, 449; 528/33, 37, 28, 25, 29, 12, 23; 525/474

[56] References Cited

U.S. PATENT DOCUMENTS

| | | | |
|---|---|---|---|
| 2,381,137 | 8/1945 | Patnode et al. | 260/462 |
| 2,381,138 | 8/1945 | Patnode et al. | 260/462 |
| 2,898,361 | 8/1959 | Barnes, Jr. et al. | 260/448.8 |
| 3,083,219 | 3/1963 | Anderson | 260/448.8 |
| 3,426,057 | 2/1969 | Kanner | 260/448.2 |
| 3,652,629 | 3/1972 | Fort et al. | 260/448.2 |
| 4,160,775 | 7/1979 | Schilling | 260/448.2 |
| 4,576,999 | 3/1986 | Eckberg | 556/445 |
| 4,590,224 | 5/1986 | Frisch, Jr. | 528/23 |

OTHER PUBLICATIONS

Chemical Abstracts, vol. 95, 62944f.
Noll, W., *Chem. and Tech. of Silicones*, Academic Press, N.Y., 1968.
Vorankov, M. G., et al., "The Siloxane Bond", Plenum Press, N.Y. (1978).
Kantor, S. W., et al., *JACS*, 76, 5190 (1954).
Hurd, D. T., *JACS*, 77, 2998 (1955).
Grubb, W. T., et al., *JACS*, 77, 1405 (1955).
Riffle, et al., "Elast. Polysil. Modifiers for Epoxy Networks", *Epoxy Resin Chem. II*, Bauer (ed), ACS Symp. Ser. 221, WA, DC (1983).
Yilgor, I., et al., "Reactive Difunctional Siloxane Oligomers: Synthesis & Characterization", *Reactive Oligomers*, (Harris & Spinelli, eds.), *ACS Symp. Ser.* 282, WA, DC (1985).
Riffle, J. S., *Ph.D. Thesis*, Virginia Inst. of Technology, (3/81).
Flory, P. J., *Principles of Polymer Chemistry*, Cornell University Press, Ithaca, N.Y., 1953.
Odian, G., *Principles of Polymers*, McGraw-Hill, N.Y. (1970).
Knoth, W. H., et al., *JACS*, 80, 4106 (1958).
Smetankina, N. P., et al., "*Physical Chem. of Urethanes*", Technomic Pub. Co., Inc., Westport, Conn. (1975), pp. 45–49.
Speier, *JACS*, 79, 974 (1957).
Yilgor, I., et al., *Reactive Difunctional Siloxane Oligomers*, ACS Symposium Series, 282, WA, D.C. (1985), (Harris & Spinelli, eds.).
Madec, P. J., et al., *J. Polym. Sci. Chem.*, 16, 3165–3172 (1978).

Primary Examiner—Melvyn I. Marquis
Attorney, Agent, or Firm—Flehr, Hohbach, Test, Albritton & Herbert

[57] ABSTRACT

Hydroxyl-functional disiloxanes and hydroxyl-functional polysiloxane oligomers are provided which contain hydroxyl groups bound to the silicon via Si—C bonds. These compounds may be crosslinked to form polysiloxane networks having improved mechanical strength or reacted to form linear, siloxane containing block copolymers.

20 Claims, No Drawings

HYDROXYL-FUNCTIONAL DISILOXANES AND POLYSILOXANE OLIGOMERS

The present invention provides novel hydroxyl-functional disiloxanes and hydroxy-functional polysiloxane oligomers, and methods for preparing same.

BACKGROUND OF THE INVENTION

Polysiloxane copolymers and networks are desirable because they possess a variety of unique and superior properties. For example, polysiloxane films and coatings provide low energy surfaces associated with the following properties: low coefficients of friction, longer wear life, biocompatibility, good releasing properties from adhesive surfaces and/or mold surfaces, and good antiblocking and lubricating properties usable for textile coatings and fiber spinning resins. Polysiloxane sealants and adhesives also exhibit resistance to degradation by ultraviolet radiation, have excellent flexibility at low temperatures while retaining stability at high temperature, are impervious to water and may be cured by convenient and economical methods.

However, a disadvantage to presently available crosslinked polysiloxanes for the above applications is their relatively poor mechanical strength. The low glass transition temperature coupled with the low intermolecular forces of presently available crosslinked polysiloxanes, provide no mechanism for the attainment of mechanical strength. On the other hand, polyurethane elastomers possess excellent mechanical properties, associated with their high degree of hydrogen bonding.

It would thus be desirable to provide a class of polysiloxanes retaining the desirable properties of crosslinked polysiloxane elastomers with improved mechanical properties.

The present invention provides tetrafunctional hydroxyl polysiloxane oligomers, having the desirable properties of polysiloxanes, which, however, can be cured with diisocyanates to form hydrolytically stable polysiloxane networks with improved mechanical properties. At least part of this improved mechanical strength is attributable to the hydrogen bonding interactions associated with the urethane bond. Furthermore, no volatile products are involved in the curing reaction.

The present invention further provides a class of difunctional hydroxyl polysiloxane oligomers which are useful to produce block copolymers for such materials as, for example, polysiloxane containing polyurethanes, polyesters, polycarbonates, and polysulfones. Although both the difunctional and tetrafunctional hydroxyl polysiloxane oligomers of the invention may form networks if reacted with multifunctional chain extenders, the tetrafunctional polysiloxanes are preferable for this purpose.

The difunctional hydroxy polysiloxane oligomers of the invention are useful for the production of polysiloxane/polycaprolactone block copolymers and for the synthesis of polysiloxane containing polyurethanes, polycarbonates, polyesters, polysulfones. The difunctional hydroxy polysiloxane copolymers are particularly useful in cases where both the properties of a hard block (a polyurethane block, a polycarbonate block, and the like) are needed and the properties of polysiloxane are needed. Among such polysiloxane properties are low energy surfaces, biocompatible polymers, high gas permeabilities, resistance to plasma etching, good UV stability, low temperature flexibility, thermally stable elastomers, etc., coupled with excellent mechanical properties.

The difunctional hydroxy polysiloxane oligomers are further useful for the polymerization of ring-opening monomers which would be initiated by hydroxyl groups or derivatives of hydroxyl groups. This would include initiation of lactones, epoxy groups, anhydride/epoxy mixtures. Examples of lactones which may be initiated for polymerization include epsilon-caprolactone, epsilon-methyl caprolactone, delta-valerolactone. Examples of epoxides include ethylene oxide, propylene oxide, styrene oxide, epichlorohydrin, allyl glycidyl ether. Examples of anhydride/epoxy mixtures include maleic anhydride/ethylene oxide, phthalic anhydride/maleic anhydride/propylene oxide, and phthalic anhydride/maleic anhydride/ethylene oxide.

It is believed that polysiloxanes having improved mechanical strength have not been heretofore formed or taught by the prior art because of at least the following two problems. Firstly, heretofore the molecular weight of the hydroxyl terminated polysiloxane blocks wherein the hydroxyl groups are bonded to the silicon via hydrolytically stable Si—C bonds were not facilely controlled. Since mechanical properties are dependent upon the block lengths in the networks, the ability to control the block lengths is important. Secondly, while a hydroxyl-terminated polysiloxane might be desirable for forming a polysiloxane network, the art taught that terminal hydroxyl groups, in the presence of strong acids used for forming polysiloxanes by redistribution reactions, will dehydrate (See *J. Polym. Sci.*, A-1, 4, 2325 (1966)). Consistent with our results obtained using hydroxybutyl terminated siloxane dimers and oligomers in the presence of strong acid catalysts, Speier, et al. (J. L. Speier, M. P. David, and B. A. Eynon, *J.O.C.*, 25, 1637 (1960)) describe the dehydration mechanism of 1,3-bis(hydroxypropyl)tetramethyldisiloxane as cyclization by attack of the hydroxyl group on the terminal silicon atom. This backbiting reaction thus removes the functional end groups in the equilibration reactions from availability for further reaction, therefore making the molecular weights and functionalities of the resultant polysiloxane oligomers uncontrollable.

The present invention provides hydroxyl-functional polysiloxane oligomers with the hydroxyl groups attached to the terminal silicon atoms via hydrolytically stable Si-C bonds which can be formed in a way to control their molecular weight to desired parameters, without the problem of the backbiting reaction.

It is therefore an object of the present invention to provide hydroxyl-functional disiloxanes consistent with the above described structures which may be expanded by siloxane redistribution reactions to hydroxyl-functional polysiloxane oligomers.

It is another object of the present invention to provide the difunctional hydroxyl polysiloxane oligomers produced in a controlled manner to desired molecular weights, which are useful to synthesize linear, siloxane-containing, thermoplastic and elastomeric block copolymers.

It is a further object of the present invention to provide novel hydroxyl-functional polysiloxane oligomers which may be networked into polysiloxane compositions having improved mechanical strength.

It is a further object of the present invention to provide a method for forming these polysiloxane oligomers having hydroxy-functional groups using acidic or basic conditions without encountering th problem of the backbiting reaction.

Additional objects, advantages and novel features of the present invention will be set forth in part in the following description and in part will become apparent to those skilled in the art upon examination of the following, or may be learned by practice of the invention. The objects and advantages of the invention may be realized and obtained by means of the instrumentalities and combinations particularly pointed out in the appended claims.

SUMMARY OF THE INVENTION

The present invention provides difunctional and tetrafunctional hydroxycarbyl terminated disiloxanes which are more sterically hindered than presently available materials and which contain primarily secondary hydroxyl groups whereas presently available materials have primary hydroxyl groups. Disiloxanes according to the invention may react to form polysiloxane oligomers in the presence of both acidic or basic catalysts and are stable to acidic type conditions necessary for acid catalyzed equilibration reactions whereas presently available materials are not. Therefore, the present invention provides a method to control the molecular weight and functionality of hydroxyl terminated oligomers which heretofore has not been accomplished. The novel hydroxy-functional disiloxane according to the present invention also may be equilibrated with basic catalysts which thus is an advantage over the presently available materials. Using presently available materials, the terminal hydroxyl group (usually a primary hydroxyl group) attacks a silicon (thereby forming a Si—O—C bond). Hence, there is no functionality or molecular weight control and the resultant oligomers are not hydrolytically stable. The presence of Si—O—C bonds is not desirable since these types of bonds are well known to be hydrolytically unstable (see W. Noll, *Chemistry and Technology of Silicones*, Academic Press, N.Y., (1968), and M. G. Voronkov, V. P. Mileshkevich, and Y. A. Yuzhelevskii, The Siloxane Bond, Plenum Press, N.Y., (1978)).

A known method of preparing difunctional, hydroxyl-functional polysiloxane oligomers is to react a hydroxyl-functional disiloxane and a cyclic polysiloxane:

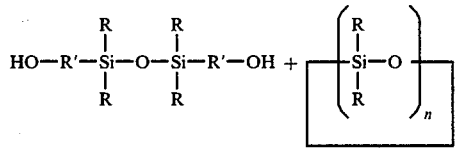

wherein R is alkyl or aryl and R' is alkyl or aryl. In most circumstances, R' is such that the terminal groups are primary hydroxyl groups. The products, if the reaction proceeds as desired, are difunctional, hydroxyl-terminated polysiloxane oligomers:

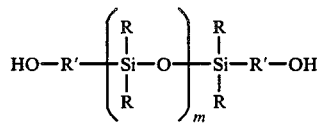

wherein m may be controlled. The molecular weight of the oligomeric products is normally controlled by the ratio of amount of disiloxane to the amount of starting cyclic polysiloxane.

This reaction of difunctional disiloxanes and cyclic siloxanes to produce polysiloxanes is commonly known as an equilibration or redistribution type reaction and is well known in the art. See, for example, W. Noll, *Chemistry and Technology of Silicones*, Academic Press, N.Y., (1968), S. W. Kantor, W. T. Grubb and R. C. Osthoff, JACS, 76, 5190 (1954), D. T. Hurd, JACS, 77, 2998 (1955), W. T. Grubb, and R. C. Osthoff, JACS, 77, 1405 (1955). The same type of reaction applied to functional disiloxanes has also been described (J. S. Riffle, Ph.D. thesis, Va. Tech., Mar., 1981, J. S. Riffle, I. Yilgor, C. Tran, G. L. Wilkes, J. E. McGrath, and A. K. Banthia, Elastomeric Polysiloxane Modifiers for Epoxy Networks in *Epoxy Resin Chemistry II*, R. S. Bauer, Ed., ACS Symposium Series #221, Washington D. C., 1983, I. Yilgor, J. S. Riffle, and J. E. McGrath, Reactive Difunctional Siloxane Oligomers: Synthesis and Characterization, in *Reactive Oligomers*, F. W. Harris and H. J. Spinelli, Eds., ACS Symposium Series #282, Washington D. C., 1985).

For the production of linear polysiloxanes to be further reacted to form block copolymers via condensation polymerization, in a redistribution reaction, it is necessary that the functionality (i.e., the number of carbofunctional hydroxyl groups per chain) of the oligomers be as close as possible to 2 in order to achieve high molecular weight block copolymers (such as in polyurethanes) (see P. J. Flory, *Principles of Polymer Chemistry*. Cornell University Press, Ithaca, N.Y., 1953, G. Odian, *Principles of Polymerization*, McGraw-Hill, N.Y., (1970)). The functionality of the polysiloxane oligomers will be no closer to 2 than the starting disiloxane but also, the redistribution reaction in which the polysiloxane oligomer is produced must be done under conditions wherein the functionality of the disiloxane remains 2. It would thus be desirable to be able to control the molecular weight and functionality of the oligomers very precisely.

Furthermore, in the presence of strong acids used for polysiloxane redistribution reactions, the hydroxyl-terminated disiloxane structures partially cyclize via attack of the hydroxyl group on the terminal silicon atom in the polymer backbone (a backbiting reaction) (in the case of using 1,3-bis(γ-hydroxybutyl)tetramethyldisiloxane, this reaction produces 1,1-dimethyl-1-sila-2-oxacyclohexane). (Also, see *J. Polym. Sci.*, A-1, 4 (9), 2325 (1966), and J. L. Speier, M. P. David, and B. A. Eynon, *J.O.C.*, 5, 1637 (1960)). This serves to remove the functional endgroups from the reaction. Hence, molecular weights and functionalities of the resultant oligomers are not controllable. In the presence of basic catalysts under appropriate equilibration conditions, alkoxyl anions produced via reaction of terminal hydroxyl groups with the basic catalyst attack the growing siloxane chain, thereby producing hydrolytically unstable Si—O—C bonds in the chain. (For further explanation of this, see *Reactive Oligomers*, F. W. Harris and H. J. Spinelli, ACS Symposium Series #282, Washington D.C., 161–174, (1985)). Since the desired endgroups are also consumed in this reaction, this route also yields oligomers without the desired molecular weight control.

Thus it is an advantage of the present invention to provide a novel general route to the synthesis of hydroxy functional disiloxanes, which are stable under the equilibration conditions described above.

The present invention also provides novel hydroxyl-functional disiloxanes of the formula IIA:

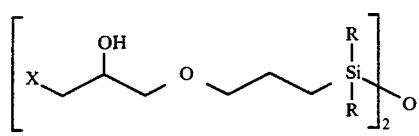
(IIA)

wherein X is —OR' or —NR$_2$R$_3$ and R', R$_2$, and R$_3$ are independently hydrogen, alkyl of 1 to 4 carbon atoms, aryl of 6 to 10 carbon atoms, or fluoroalkyl of 1 to 4 carbon atoms or R$_2$ and R$_3$ are joined to form a heterocyclic ring; and R is alkyl of 1 to 4 carbon atoms, fluoroalkyl of 1 to 4 carbon atoms or aryl of 6 to 10 carbon atoms.

The present invention further provides hydroxyl-functional polysiloxane oligomers of the formula V:

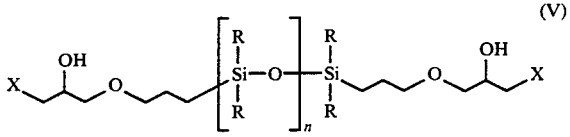
(V)

wherein R and X are as defined above and n is an integer from 1 to about 5000.

The present invention further provides methods for making compounds of the formulas IIA and V.

DESCRIPTION OF THE INVENTION

The novel disiloxanes and polysiloxanes according to the present invention may be provided by initially preparing an intermediate of the formula I.

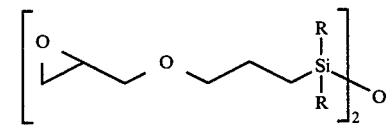
(I)

The epoxy-terminated disiloxane (I) may be prepared according to the following scheme

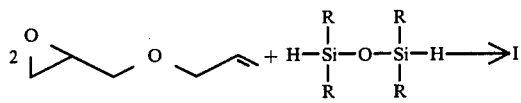

whichis a reactin of allylglycidylether with a tetraalkyl disiloxane in the presence of chloroplatinic acid according to conditions taught in *J. Polym. Sci., Chem.*, 16, 3165–3172 (1978). The epoxy-terminated disiloxane (I) may then be reacted with a nucleophilic agent, X, such as an alcohol, ammonia, a secondary amine, or water, in the presence of a catalytic amount of a strong acid to produce the following mixture of products.

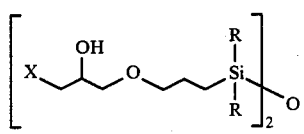
(IIA)

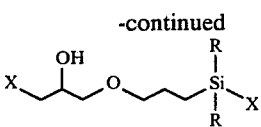
(IIB)

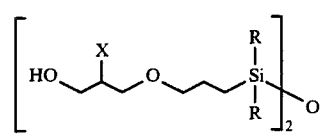
(IIIA)

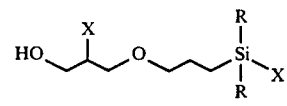
(IV)

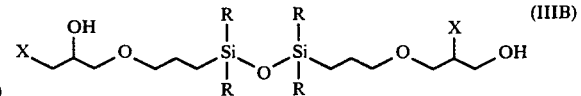
(IIIB)

Although all of the above products may be present in the reaction mixture, the most significant proportion of the products will consist of the compound of the formula IIA, and the predominant impurity will be compounds of the formula IIB. The remaining compounds IIIA, IIIB and IV will be present in trace amounts. However, by hydrolyzing the mixture with, for example, aqueous hydrochloric acid, the compounds IIB and IV will be converted to IIA, IIIA and IIIB. The final product will therefore consist primarily of the disiloxane IIA, with lesser amounts of the disiloxanes IIIA and IIIB. The presence of small amounts of IIIA and IIIB will not substantially affect the further processing of the mixture to polysiloxanes for the intended purposes set forth herein.

The preferred compounds of the formula IIA are those wherein X is OR' and R' is hydrogen, alkyl of 1 to 4 carbon atoms, or aryl of 6 to 10 carbon atoms. Another preferred class of compounds of the formula IIA is the class wherein X is NR$_2$R$_3$ and R$_2$R$_3$ are joined to form a heterocyclic ring. A preferred group is the nexamethyleneimine,

—N(CH$_2$)$_6$.

In the formula V, n is preferably from 2 most preferably from 5 to 150.

The groups R', R$_2$, R$_3$ and R include linear and branched alkyl and fluoroalkyl groups. Examples include methyl, ethyl, isopropyl, n-propyl, n-butyl, sec-butyl, t-butyl, trifluoromethyl, 1,1,2,2-tetrafluoroethyl and trifluoropropyl. Exemplary aryl groups include phenyl, naphthyl and benzyl. In the case of R$_2$ and R$_3$, the term alkyl of 1 to 4 carbon atoms as used herein includes instances where R$_2$ and R$_3$ are joined to form a heterocyclic ring, whereby the ring may contain from 2 to 8 carbon atoms. Two preferred classes are those wherein R$_2$ and R$_3$ are independently alkyl of 1 to 4 carbon atoms and wherein R$_2$ and R$_3$ are both hydrogen.

It is an important feature of the present invention that the disiloxane (IIA) having terminal secondary hydroxy groups can be expanded to polysiloxanes by use of the conventional polysiloxane redistribution reaction.

Thus, equilibration of the disiloxane IIA with octamethylcyclotetrasiloxane (D4) or other cyclic polysiloxanes, in the presence, for example, of about 0.1% by weight of a trifluoromethane sulfonic acid catalyst at 65° C., will provide polysiloxane oligomers of the formula V of controlled molecular weights possessing hydroxyl groups on each end of the oligomer. The size of the siloxane blocks, as determined by the integer n, may be controlled by the amount of cyclic polysiloxane used in the redistribution reaction.

A further important feature of the present invention is that the redistribution reaction may be conducted in the presence of a strong acid catalyst without the undesired side reaction of the terminal hydroxy groups attacking the siloxane backbone of the oligomer.

A particularly preferred class of disiloxanes are of the formula IIC, which may be converted by the redistribution reaction to polysiloxanes of the formula VA.

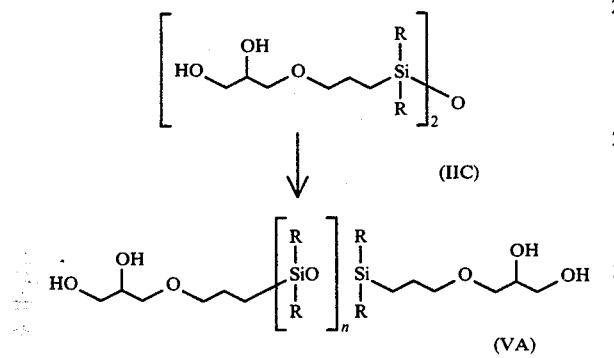

The tetrahydroxy-functional polysiloxane oligomers of the formula (VA) may be crosslinked in bulk with multifunctional isocyanates, such as p,p'-diisocyanatodicyclohexylmethane, 1,6-hexamethylenediisocyanate, isophorone diisocyanate, p,p'-diisocyanatediphenylmethane, 2,4- or 2,6-tolylene diisocyanate, optionally in the presence of a polyurethane catalyst, at about 20°–100° C. to yield a crosslinked polysiloxane network with improved mechanical strength.

The following examples are presented to help in the better understanding of the present invention and for purposes of illustration. The examples, are not to be construed as limiting the invention to the precise form disclosed or to limit the scope of the invention in any manner or means.

EXAMPLE 1

Procedure for the synthesis of
1,3-bis(glycidoxypropyl)tetramethyldisiloxane(I,R=methyl)

A chloroplatinic acid catalyst solution was prepared as follows: 0.518 g hydrogen hexachloroplatinate hydrate was dissolved in 50 ml allyl-glycidyl ether. A round bottomed flask equipped with a nitrogen purge and agitation was charged with 700 g (6.133 moles) allyl glycidyl ether and 6.16 g of the chloroplatinic acid catalyst solution described above and heated to 25° C. for 1 hour. 316.4 g (2.361 moles) tetramethyldisiloxane was added in portions as follows. 3–4% of the total amount was added in each increment. Each increment was fully reacted as evidenced by the disappearance of the Si—H absorption in the IR at approximately 2120 cm$^{-1}$ prior to another addition of tetramethyldisiloxane. In this manner, the exotherm was controlled to less than 45° C. The excess allyl glycidyl ether was vacuum stripped at ~50° C./0.5 mm. Gel permeation chromatography showed a single sharp peak. $^1$H NMR yielded a singlet at delta 0.1 (6 protons), multiplet at delta 0.46–0.66 (2 protons), multiplet at delta 1.46–1.80 (2 protons), multiplet at delta 2.46–2.76 (2 protons), multiplet at delta 3.00–3.17 (1 proton), and a multiplet at delta 3.23–3.76 (6 protons) (delta given in ppm from TMS).

EXAMPLE 2

Preparation of Tetrahydroxy-Functional Disiloxane (IIC)

A round bottomed flask equipped with a nitrogen purge and agitation is charged with 165 g (0.91 equiv.) 1,3-bis(glycidoxypropyl)tetramethyldisiloxane, 330 g (18.3 equiv.) water, and approximately 900 ml acetone and heated to reflux (55–56° C.). 50 μl trifluoromethanesulfonic acid are added and the temperature is maintained for 72 hours. The strong acid catalyst is neutralized with 2 ml 1N KOH (in methanol or aqueous), 4 ml conc. HCl is then added and the solution is refluxed for 3 additional hours. Acetone and water are stripped under vacuum and compound IIC is extracted with dichloromethane. Dichloromethane is removed under vacuum, the disiloxane is further dried with MgSO$_4$ and residual water is vacuum stripped.

The gel permeation chromatogram yields a single, sharp peak.

EXAMPLE 3

Procedure for the synthesis of the methanol capped 1,3-bis-(glycidoxypropyl)tetramethyldisiloxane (($CH_3$—O—$CH_2$—CH(OH)—$CH_2$—O—($CH_2$)$_3$—Si($CH_3$)$_2$)$_2$—O (IIA. R=methvl. X=OCH$_3$)

A nitrogen purged reaction vessel with agitation is charged with 130 g (0.72 equiv.) of 1,3-bis(glycidoxypropyl)tetramethyldisiloxane, 580 g (18.12 equiv.) methanol and 10 μl (1.13×10$^{-5}$ equiv.) trifluoromethanesulfonic acid. The reaction mixture is refluxed (approximately 65° C.) for 7–8 hours. The trifluoromethanesulfonic acid catalyst is neutralized with 1 ml of 1N. KOH in methanol. In order to convert the structure IIB to IIA, 14 ml 1N aqueous HCl is added and the mixture is refluxed for 2 additional hours. The methanol and water present are removed under vacuum. The product is vacuum distilled at approximately 200° C./0.5 mm. Yield is approximately 80%. $^1$H NMR yields a singlet at delta 0.13 (6 protons), a multiplet at delta 0.46–0.66 (2 protons), a multiplet at delta 1.50–1.83 (2 protons), a singlet at delta 2.83 (1 proton), multiplet at delta 3.33–3.76 (9 protons), and a multiplet at delta 3.86–4.17 (1 proton). Delta is given in ppm from TMS.

EXAMPLE 4

Preparation of a polysiloxane oligomer of controlled molecular weight with two hydroxyl groups on each terminal group: Mn≃2000 o/mole A nitrogen purged reaction vessel with agitation is charged with 40.0 g (0.2010 equivalents) of the tetrahydroxyfunctional disiloxane of example 2 and 170.0 g octamethylcyclotetrasiloxane and heated to 65° C.–70° C. The mixture remains immiscible. Then, 0.2 ml (2.261×10$^{-3}$ moles) trifluoromethanesulfonic acid catalyst is added and a 65°14 70° C. temperature is maintained for 24 hrs. The mixture becomes homogeneous as the reaction proceeds. The trifluoromethanesulfonic acid catalyst is neutralized via addition of 4.0 ml ($4\times10^{-3}$ moles) 1N methanolic potassium hydroxide and stirring at 65°–70° C. for 10 minutes. Subsequently, the excess potassium hydroxide is neutralized with 2 ml ($2\times10^{-3}$ moles) 1N HCl in isopropanol. The cyclic siloxanes are stripped from the reaction mixture under vacuum at ~130° C./1 mm. Yield ~85%.

EXAMPLE 5A

Preparation of a crosslinked polysiloxane network by reaction of a 2000 g/mole molecular weight tetrahydroxyfunctional polysiloxane oligomer with a diisocyanate Fifteen g of the polysiloxane oligomer, 3.61 g 4,4'-diisocyanatodicyclohexylmethane, and 0.015 g stannous octoate were weighed into a 100 ml beaker, stirred well to obtain a cloudy mixture, and heated in an oven to 75° C. The solution cleared within 5 minutes under these conditions. Subsequently, the reaction mixture was poured into a glass mold and cured at 75° C. for 20 more minutes to produce a transparent, strong, crosslinked elastomer.

EXAMPLE 5B

Preparation of a crosslinked polysiloxane network by reaction of a 2000 g/mole molecular weight tetrahydroxyfunctional polysiloxane oligomer with a diisocyanate in the absence of a catalyst 15.02 g of the polysiloxan oligomer and 3.62 g 4,4'-diisocyanatodicyclohexylmethane were weighed into a 100 ml beaker and thoroughly mixed to produce a cloudy solution. The mixture was heated in an oven at 75° C. Within 40 minutes, the solution became transparent and homogeneous. It was poured into a glass mold and cured at 75° C. for 20 hours to produce a strong, transparent, highly crosslinked polysiloxane elastomer.

EXAMPLE 6

Redistribution reaction of methanol-capped disiloxane to form polysiloxane oligomer For an oligomer of approximately 3000 g/mole number average molecular weight, a nitrogen purged reaction vessel with agitation is charged with 14.23 g (0.067 equiv.) of the product from EXAMPLE 3 and 95.77 g octamethylcyclotetrasiloxane ($D_4$) and heated to 65° C. Trifluoromethanesulfonic acid catalyst (60$\mu$l) is added and the reaction temperature is maintained for 20 hours. Subsequently, the trifluoromethanesulfonic acid catalyst is neutralized with 1 ml 1N KOH in methanol (approximately 0.3 meq. excess KOH), then the remaining potassium hydroxide is neutralized with 0.4 ml 1N HCl (in either methanolic or isopropanolic solution). The added alcohol and equilibration cyclic products are removed by vacuum stripping at approximately 130° C./1 mm until the distillate ceases. After filtration of the salts formed in the neutralization, 95 g of a clear, colorless, slightly viscous polysiloxane oil was obtained. Gel permeation chromatography showed a unimodal, approximately gaussian molecular weight distribution with a number average molecular weight of approximately 2700 g/mole.

EXAMPLE 7

Comparative example of attemoted redistribution reaction of a primary hydroxyl-terminated disiloxane For a desired number average molecular weight of approximately 2200 g/mole, a nitrogen purged reaction vessel is charged with agitation with 9.50 g (0.0341 moles) 1,3-bis(7-hydroxybutyl)tetramethyldisiloxane and 65.50 g octamethylcyclotetrasiloxane and heated to 60°–65° C. Subsequently, 44 $\mu$l trifluoromethanesulfonic acid catalyst is added and the reaction temperature is maintained for 21 hours. The trifluoromethanesulfonic acid catalyst is neutralized with 0.8 ml 1N KOH in methanol (approximately 0.3 meq. excess), then, subsequently the excess KOH is neutralized with 0.4 ml 1N HCl (in methanol or isopropanol). The added alcohol and equilibration side products are removed by vacuum distilling at approximately 130° C./1 mm until the distillate ceases. Gel permeation chromatography shows the formation of a large amount of 1,1-dimethyl-1-sila-2-oxacyclohexane early in the reaction, which is maintained throughout the reaction. To confirm the occurrence of this undesired side reaction the stability of 1,3-bis($\gamma$-hydroxyl)tetramethyldisiloxane under the acid catalyzed equilibration conditions was tested. The following test shows that 1,3-bis($\gamma$-hydroxybutyl)tetramethyldisiloxane reacts in the presence of a catalytic amount of trifluoromsthanesulfonic acid to form large amounts of 1,1-dimethyl-1-sila-2-oxacyclohexane. Hence, this dimer is not stable to the reaction conditions. 8.36 g (0.030 moles) samples of 1,3-bis($\gamma$-hydroxybutyl)disiloxane together with 3 $\mu$l trifluoromethanesulfonic acid catalyst were charged to a series of reaction vessels and heated to various temperatures: 45°–50° C., 60°–65° C., and 80°–85° C. Samples were taken from the reaction mixtures at various times and the reactions were followed with $^1$H NMR. An equilibrium is established at all 3 temperatures at approximately 30 wt. % 1-dimethyl-1-sila-2-oxacyclohexane. $^1$H NMR of 1,1-dimethyl-1-sila-2-oxacyclohexane yields a singlet at delta 0.20 (6 protons), a triplet at delta 0.59–0.73 (2 protons), a multiplet at delta 1.46–2.00 (4 protons), and a triplet at delta 3.83-3.96 (2 protons). $^1$H NMR of 1,3-bis($\gamma$-hydroxybutyl)tetramethyldisiloxane yields a singlet at delta 0.10 (6 protons), a triplet at delta 0.50–0.66 (2 protons), a multiplet at delta 1.25–1.83 (4 protons), a broad singlet at delta 2.83 (1 proton), and a triplet at delta 3.56–3.69 (2 protons). Delta is given in PPM from TMS.

EXAMPLE 8

Synthesis of the hexamethyleneimine capped 1,3-bis(glycidoxypropyl)tetramethyldisiloxane (IIA. R=methyl. X=—N (CH$_2$)$_6$)

A nitrogen purged, round bottomed flask equipped with agitation was charged with 18.17 g (100 meq.) 1,3-bis(glycidoxypropyl)tetramethyldisiloxane (I) and 1.12 g hexamethyleneimine (112 meq.) and heated to 65°–70° C. The temperature was maintained for 2.5-3 hours. The excess hexamethyleneimine was removed under vacuum at 100°14 120° C.

EXAMPLE 9

Equilibration reaction of the hexamethyleneimine capped disiloxane and octamethylcyclotetrasiloxane to form a polysiloxane oligomer For an oligomer of approximately 2200 g/mole number average molecular weight, a nitrogen-purged, round-bottomed flask with agitation is charged with 56.17 g of the product from EXAMPLE 8 and 163.90 g octamethylcyclotetrasiloxane and heated to 80°-85° C. Then 0.11 g tetramethylammonium hydroxide pentahydrate is added and the temperature is maintained for 26.5 hours. Subsequently, the temperature is raised to 140°-150° C. and maintained for approximately 3 hours in order to decompose the catalyst and volatilize its degradation products. The cyclic products are vacuum distilled at 135° C./approx. 1 mm for approximately 3 hours or until the distillate ceases. 198 g of a viscous, pale yellow oligomer is produced. Gel permeation chromatography shows a unimodal, approximately gaussian molecular weight distribution with a number average molecular weight of approximately 2000 g/mole.

We claim:

1. A compound according to the formula

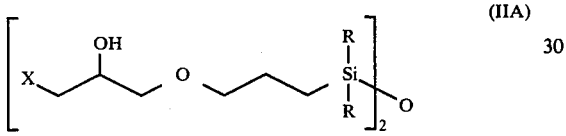

wherein R is alkyl of 1 to 4 carbon atoms, fluoroalkyl of 1 to 4 carbon atoms, or aryl of 6 to 10 carbon atoms; and X is —OR' or —NR$_2$R$_3$ wherein R', R$_2$, and R$_3$ are independently hydrogen, alkyl of 1 to 4 carbon atoms, aryl of 6 to 10 carbon atoms or fluoroalkyl of 1 to 4 carbon atoms, or R$_2$R$_3$ are joined to form a heterocyclic ring 2. A compound according to claim 1 wherein X is OR'.

3. A compound according to claim 2 wherein R' is alkyl of 1 to 4 carbon atoms.

4. A compound according to claim 3 wherein R' is methyl.

5. A compound according to claim 2 wherein R is alkyl.

6. A compound according to claim 5 wherein R is methyl.

7. A compound according to claim 1 wherein X is NR$_2$R$_3$.

8. A compound according to claim 7 wherein R$_2$R$_3$ are joined to form a heterocyclic ring.

9. A compound according to claim 8 wherein R$_2$ and R$_3$ are joined to each other and to the nitrogen atom to form a hexamethyleneimino group.

10. A compound according to claim 7 wherein R$_2$ and R$_3$ are independently alkyl of 1 to 4 carbon atoms.

11. A compound according to claim 7 wherein R$_2$ and R$_3$ are hydrogen.

12. A compound according to claim 7 wherein R is alkyl.

13. A compound according to claim 12 wherein R is methyl.

14. A compound according to the formula

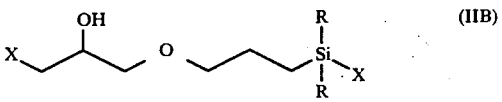

wherein R is alkyl of 1 to 4 carbon atoms, fluoroalkyl of 1 to 4 carbon atoms, or aryl of 6 to 10 carbon atoms; and X is —OR' or —NR$_2$R$_3$ wherein R', R2, and R$_3$ are independently hydrogen, alkyl of 1 to 4 carbon atoms, aryl of 6 to 10 carbon atoms or fluoroalkyl of 1 to carbon atoms.

15. A compound according to claim 1 wherein X is OR' and R' is hydrogen.

16. A compound according to claim 15 wherein R is alkyl.

17. A compound according to claim 16 wherein is methyl.

18. A compound according to the formula

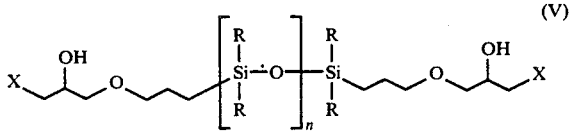

wherein R is alkyl of 1 to 4 carbon atoms, fluoroalkyl of 1 to 4 carbon atoms, or aryl of 6 to 10 carbon atoms; X is —OR' or —NR$_2$R$_3$ and R', R$_2$ and R$_3$ are independently hydrogen, alkyl of 1 to 4 carbon atoms, aryl of 6 to 10 carbon atoms or fluoroalkyl of 1 to 4 carbon atoms, or R$_2$R$_3$ are joined to form a heterocyclic ring; and n is an integer from 1 to 5,000.

19. A compound according to claim 18 wherein R is alkyl and n is from 2 to 300.

20. A method for forming a polysiloxane according to the formula

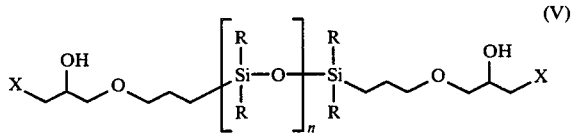

wherein R is alkyl of 1 to 4 carbon atoms, fluoroalkyl of 1 to 4 carbon atoms, or aryl of 6 to 10 carbon atoms; X is —OR' or —NR$_2$R$_3$ and R', R$_2$ and R$_3$ are independently hydrogen, alkyl of 1 to 4 carbon atoms, aryl of 6 to 10 carbon atoms or fluoroalkyl of 1 to 4 carbon atoms, or R$_2$R$_3$ are joined to form a heterocyclic ring; and n is an integer from 1 to 5000 comprising the steps of reacting a compound of the formula

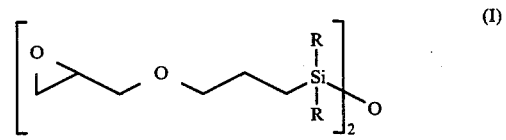

with a nucleophilic agent X: to produce a compound of the formula

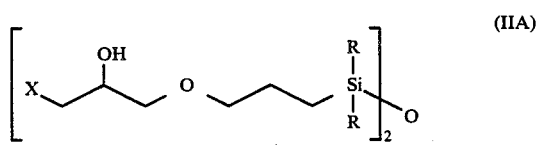

and treating the compound of the formula IIA with a cyclic polysiloxane in a redistribution reaction to form said polysiloxane.

* * * * *